United States Patent [19]

Gupta

[11] Patent Number: 5,436,382
[45] Date of Patent: Jul. 25, 1995

[54] ISOBUTYLENE RECOVERY PROCESS
[75] Inventor: Vijai P. Gupta, Berwyn, Pa.
[73] Assignee: Arco Chemical Technology, L.P., Greenville, Del.
[21] Appl. No.: 339,536
[22] Filed: Nov. 15, 1994
[51] Int. Cl.⁶ .............................................. C07C 1/24
[52] U.S. Cl. .................................. 585/639; 585/638; 585/640
[58] Field of Search ..................... 585/638, 639, 640

[56] References Cited

U.S. PATENT DOCUMENTS

| | | | |
|---|---|---|---|
| 3,510,538 | 5/1970 | Rosenthal | 585/639 |
| 3,665,048 | 5/1972 | Grane et al. | 585/640 |
| 4,036,905 | 7/1977 | Kornfeld | 585/639 |
| 4,155,945 | 5/1979 | Levine | 585/639 |
| 4,165,343 | 8/1979 | Levine et al. | 585/638 |
| 4,207,424 | 6/1980 | Winnick | 585/357 |
| 4,423,271 | 12/1983 | Obenaus et al. | 585/639 |
| 5,191,143 | 3/1993 | Su et al. | 585/640 |

*Primary Examiner*—Asok Pal
*Assistant Examiner*—Bekir L. Yildirim
*Attorney, Agent, or Firm*—William C. Long

[57] ABSTRACT

The present invention provides a process for producing isobutylene from a tertiary butyl alcohol purge stream comprised of tertiary butyl alcohol, water and light organics by a hydrocarbon solvent extraction of tertiary butyl alcohol, stripping of the extracted tertiary butyl alcohol from the solvent and dehydration of the stripped tertiary butyl alcohol to form isobutylene.

2 Claims, 1 Drawing Sheet

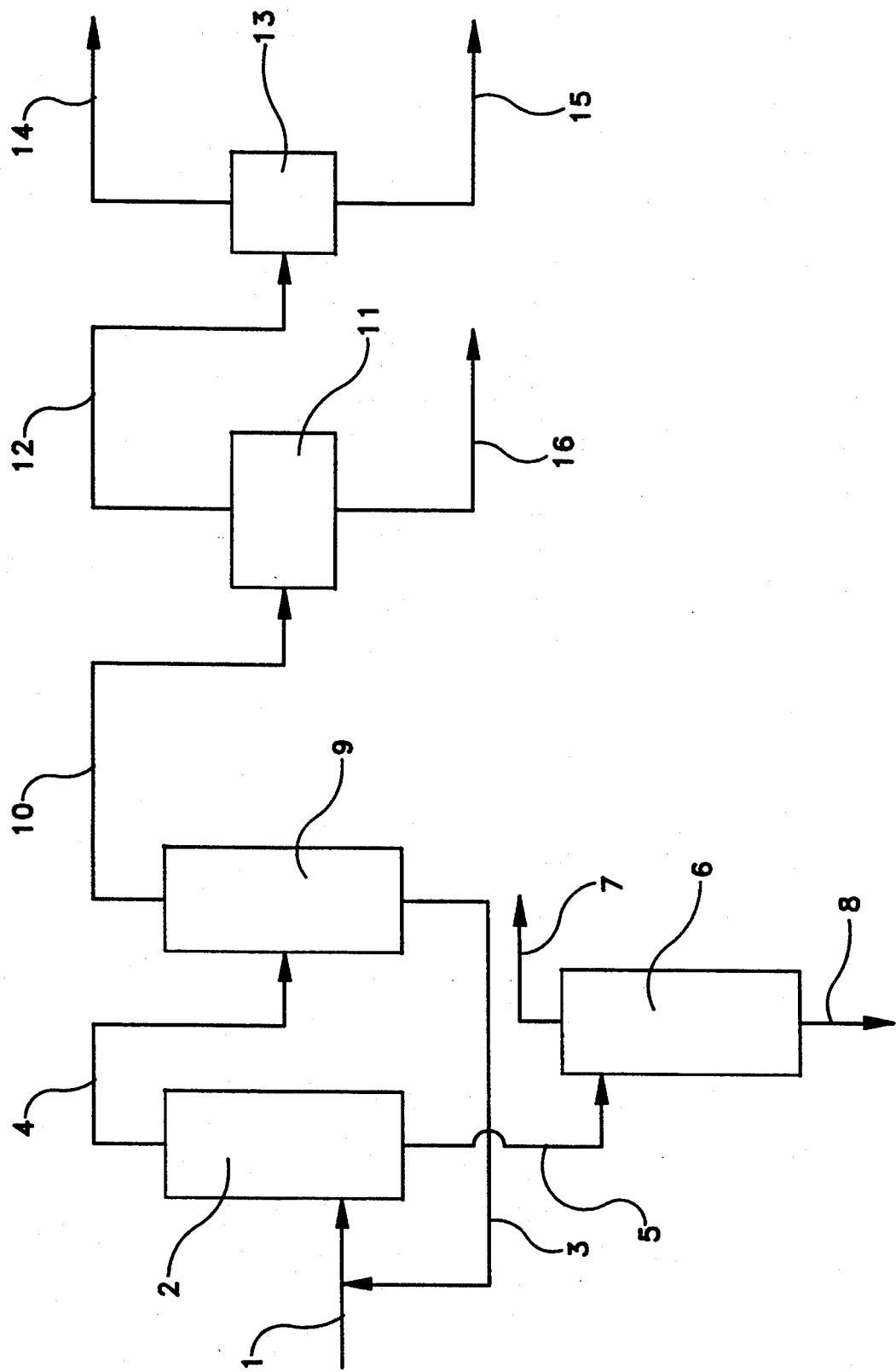

ISOBUTYLENE RECOVERY PROCESS

FIELD OF THE INVENTION

The present invention relates to the treatment of a process stream from tertiary butyl alcohol dehydration to recover additional isobutylene values therefrom by a processing sequence which comprises solvent extraction of the process stream with a hydrocarbon solvent, stripping tertiary butyl alcohol from the solvent extract and dehydrating the stripped tertiary butyl alcohol.

DESCRIPTION OF THE PRIOR ART

Process for the dehydration of tertiary butyl alcohol to isobutylene are well known. Vapor phase processes such as those described in U.S. Pat. Nos. 4,036,905, 3,665,048 and 4,207,424 are illustrative.

Liquid phase reaction systems such as those described in U.S. Pat. Nos. 3,510,538, 4,165,343 and 4,155,945 are illustrative.

Generally speaking, the isobutylene-containing product of dehydration is purified by a water scrubbing process whereby various organic materials such as tertiary butyl alcohol, acetone, methanol and the like are scrubbed from the isobutylene. It is conventional to distill the aqueous scrubber liquid to recover valuable products such as acetone therefrom and to recycle from the scrubber distillation a stream containing tertiary butyl alcohol, water and organics which is returned to the tertiary butyl alcohol dehydration.

To avoid build-up of impurities which interfere with the dehydration and/or are difficult and costly to separate from isobutylene, a portion of the recycle stream is purged and used as low grade fuel. Similarly a tertiary butyl alcohol rich purge stream is taken from tertiary butyl alcohol vaporizers to prevent heavies build up.

It would be quite advantageous if a convenient and economic process were devised to recover tertiary butyl alcohol from such purge streams and dehydrate the recovered tertiary butyl alcohol to provide additional quantities of the valuable isobutylene. The present invention provides such a process.

SUMMARY OF THE INVENTION

In accordance with the present invention, the tertiary butyl alcohol purge stream which contains tertiary butyl alcohol, water and $C_1$ to $C_4$ oxygenates (mainly alcohols and ketones) is contacted with a hydrocarbon solvent extractant whereby the tertiary butyl alcohol and oxygenates are mainly extracted from an aqueous phase, the hydrocarbon solvent is stripped of absorbed tertiary butyl alcohol and oxygenates, and the obtained mixture of tertiary butyl alcohol and oxygenates with only a low amount of water is subjected to dehydration conditions and further product isobutylene is recovered.

DESCRIPTION OF THE DRAWING

The accompanying drawing illustrates schematically practice of the invention.

DETAILED DESCRIPTION

Referring to the accompanying drawing, the tertiary butyl alcohol purge stream containing tertiary butyl alcohol, significant amounts of water and $C_1$-$C_4$ oxygenates passes via line 1 to solvent extraction column 2. A hydrocarbon solvent stream, most preferably a paraffin stream having about 8-14 carbon atoms, passes via line 3 and is combined with the tertiary butyl alcohol stream and enters solvent extraction column 2. In column 2 the hydrocarbon solvent absorbs tertiary butyl alcohol and various oxygenated materials and the organic phase passes upwardly and exits column 2 via line 4. The aqueous phase comprised of the predominance of water which is associated with the tertiary butyl alcohol purge stream passes downwardly and is removed from solvent extraction column 2 by means of line 5 and passes to stripper 6. In stripper 6 the light organics are stripped overhead and removed via line 7 while the net water is rejected from the system via line 8.

The solvent phase from solvent extraction column 2 passes via line 4 to stripping column 9. In column 9 the tertiary butyl alcohol and oxygenated materials are stripped overhead and removed via line 10. The stripped solvent is removed and passed via line 3 back to solvent extraction column 2. A small amount of make-up solvent (not shown) is provided to make up for the small losses of solvent.

The tertiary butyl alcohol and oxygenated materials pass from stripping column 9 via line 10 to dehydration zone 11 wherein the tertiary butyl alcohol is subjected to a liquid phase dehydration in order to produce supplemental quantities of valuable isobutylene product. It should be noted that vapor phase dehydration procedures are also applicable.

Vapors from the liquid phase dehydration comprised of isobutylene are removed via line 12 and passed to zone 13 from which product isobutylene vapors are recovered through line 14 and the oxygenated organic materials are separated by means of line 15 and can be employed as a low value fuel material.

A small amount of heavy material is purged from liquid phase dehydration zone 11 by means of line 16.

The tertiary butyl alcohol dehydration purge stream generally comprises by weight about 20–50% tertiary butyl alcohol, 15–40% water, 5–20% methanol, 0.5–5% acetone, 8–20% isopropanol, 1–5% methyl ethyl ketone, 1–5% secondary butanol and 5–15% isobutanol. This stream is solvent extracted with a hydrocarbon as above indicated in order to separate a predominance of the contained water which otherwise would interfere with the dehydration reaction whereby isobutylene is formed from the tertiary butyl alcohol. The solvent extraction is carried out in accordance with conventional procedures, and any hydrocarbon which is effective for the absorption of tertiary butyl alcohol and the rejection of water can be employed. Saturated hydrocarbons are preferred by reason of their low reactivity and especially preferred are paraffins and cycloparaffins having a distillation range substantially above that of tertiary butyl alcohol and which have a high capacity for tertiary butyl alcohol absorption. Most preferred are the paraffins and cycloparaffins having 9 to about 12 carbon atoms. The solvent hydrocarbon or hydrocarbon mixture preferably has a 50% distillation range of 100°–300° C., more preferably 125°–200° C.

The stripping of absorbed tertiary butyl alcohol and oxygenates from the solvent is carried out in accordance with conventional procedures, the solvent being selected on the basis of being readily separable by distillation from the absorbed materials.

The stripped tertiary butyl alcohol and organics are conveniently subjected to liquid phase dehydration by reason of the low water content, and the isobutylene is separated and ultimately recovered as vapor, thus eliminating the need for subsequent expensive distillations.

The water phase which is rejected during the hydrocarbon solvent extraction is stripped in order to separate contained organics leaving a purge water stream which is of sufficient purity as to be disposed, for example, in a biopond.

The practice of the present invention has the outstanding advantage that a normally waste stream suitable in the past only as a low grade fuel stream is conveniently and effectively treated for the production of substantial additional quantities of the valuable isobutylene product. Through practice of the designated process, efficiencies and economies of operation are achieved while the adverse polluting impact is substantially eliminated.

The following example illustrates the invention; unless otherwise stated, all amounts and percentages are be weight.

Referring to the drawing, about 650 parts/hr of a tertiary butyl alcohol feed stream passes via line 1 to solvent extraction column 2. The feed comprises about 33% tertiary butyl alcohol, 24% water, 10% methanol, 12% isobutanol, 14% isopropanol, 2% acetone, 2.5% methyl ethyl ketone, and 2.5% secondary butanol.

Also fed to extraction column 2 via line 3 is about 3285.5 parts/hr of a commercially available mainly $C_{10}$ and $C_{11}$ isoparaffin stream, ISOPAR-G of the Exxon company, which contains about 1% isobutanol from prior extractive use. In column 2 the isoparaffin stream effectively extracts tertiary butyl alcohol and other organics and the solvent extract stream is removed via line 4 at 135° F. and 30 psig and passed to stripper 9 at the rate of 3712.7 parts per hour. This stream is comprised of about 87.5% solvent, about 1% methanol, 0.2% acetone, 2.1% isopropanol, 5.4% tertiary butyl alcohol, 0.4% methyl ethyl ketone, 0.4% secondary butanol, 2.8% isobutanol and about 0.1% water.

An aqueous stream is removed from column 2 via line 5 at the rate of about 219.8 parts/hr and passes to stripper 6. This stream comprises about 69.6% water, 11.8% methanol, 1.9% acetone, 6.2% isopropanol, 6.8% tertiary butyl alcohol, a trace of methyl ethyl ketone and secondary butanol, 2.5% isobutanol and trace of isoparaffin.

In stripper 6, essentially all of the organics are stripped overhead via line 7 and this overhead is suitable as fuel or it may be further treated for recovery of the various components. The bottoms water stream is removed via line 8 and can be disposed of in a biopond.

In stripper 9, extracted organics are stripped from the paraffin solvent at 204° F. and 7 psig and removed via line 10. Solvent is removed via line 3 and is recycled to extraction column 2. A small amount of make-up solvent is added as needed (not shown).

The overhead from stripper 9 passes via line 10 to dehydration zone 11 at the rate of about 431.2 parts/hr. This stream comprises about 46.3% tertiary butyl alcohol, 16.8% isobutanol, about 3.5% each of methyl ethyl ketone and secondary butanol, about 17.9% isopropanol, about 2% acetone, about 9% methanol and about 0.7% water.

In dehydrator 11 the tertiary butyl alcohol is dehydrated in a liquid phase system at 275° F. and 60 psig using 2.5 wt % p-toluene sulfonic acid catalyst. A heavies purge is separated via line 16 at the rate of 5 parts/hr. The dehydration overhead passes at the rate of 143.9 parts/hr via line 12 to separator 13. An isobutylene stream is recovered via line 14 at the rate of 143.9 parts/hr and comprises 95.9% isobutylene.

A fuel stream is removed at the rate of 282.4 parts/hr via line 15 and this stream is suitable as a lower grade fuel stream.

I claim:

1. The process for the production of isobutylene from a tertiary butyl alcohol dehydration purge stream which contains tertiary butyl alcohol, water and $C_1$–$C_4$ oxygenated organics which comprises extracting tertiary butyl alcohol and oxygenated organics into a hydrocarbon solvent, separating the extraction phase from an aqueous phase containing the predominance of water in the tertiary butyl alcohol purge stream, stripping tertiary butyl alcohol from the hydrocarbon solvent and dehydrating the stripped tertiary butyl alcohol to form isobutylene.

2. The process of claim 1 wherein the hydrocarbon solvent is a $C_8$–$C_{14}$ paraffin solvent.

* * * * *